United States Patent
Li et al.

(10) Patent No.: US 12,319,666 B2
(45) Date of Patent: Jun. 3, 2025

(54) HYDRATE OF DIMETHYLAMINOMICHELIOLIDE FUMARATE AND PREPARATION METHOD THEREFOR AND USE THEREOF

(71) Applicants: ACCENDATECH CO. LTD., Tianjin (CN); NANKAI UNIVERSITY, Tianjin (CN)

(72) Inventors: Zhonghua Li, Tianjin (CN); Junbo Gong, Tianjin (CN); Baohong Hou, Tianjin (CN); Songgu Wu, Tianjin (CN); Yue Chen, Tianjin (CN); Chuanjiang Qiu, Tianjin (CN); Xinghua Zhu, Tianjin (CN); Jie Qi, Tianjin (CN); Guiyan Wang, Tianjin (CN)

(73) Assignees: ACCENDATECH CO. LTD., Tianjin (CN); NANKAI UNIVERSITY, Tianjin (CN)

( * ) Notice: Subject to any disclaimer, the term of this patent is extended or adjusted under 35 U.S.C. 154(b) by 504 days.

(21) Appl. No.: 17/905,127

(22) PCT Filed: Mar. 26, 2020

(86) PCT No.: PCT/CN2020/081349
§ 371 (c)(1),
(2) Date: Aug. 26, 2022

(87) PCT Pub. No.: WO2021/189343
PCT Pub. Date: Sep. 30, 2021

(65) Prior Publication Data
US 2023/0089334 A1    Mar. 23, 2023

(51) Int. Cl.
C07D 307/93    (2006.01)

(52) U.S. Cl.
CPC ........ C07D 307/93 (2013.01); *C07B 2200/13* (2013.01)

(58) Field of Classification Search
CPC .............. C07D 307/93; C07B 2200/13; C07B 2200/07; C07C 57/15; A61K 9/4866;
(Continued)

(56) References Cited

FOREIGN PATENT DOCUMENTS

| CN | 103724307 A | * | 4/2014 | ........... C07D 307/93 |
| CN | 104876899 A |   | 9/2015 | |

(Continued)

OTHER PUBLICATIONS

Bommagani, Shobanbabu et al.; "13-(N, N-Dimethylamino)micheliolide 0.08-hydrate.", Acta Crystallographica Section E Structure Reports, vol. E69, Dec. 31, 2013; pp. o1789-o1790.

*Primary Examiner* — Joseph K McKane
*Assistant Examiner* — Ashli Ariana Chicks
(74) *Attorney, Agent, or Firm* — NKL Law; Allen Xue

(57) ABSTRACT

A hydrate of dimethylaminomicheliolide fumarate has a crystal form D, is high in crystallinity, smooth in particle surface, free of coalescence, high in bulk density and good in flowability, and has good stability and good reproducibility. Its preparation method includes: under a stirring action, adding dimethylamine micheliolide and fumaric acid into a mixed solvent system having a constant temperature of 30° C.-70° C. for reaction crystallization; and filtering after the reaction is finished, and drying filtered solid at normal pressure to obtain the crystal form D of the dimethylaminomicheliolide fumarate.

11 Claims, 4 Drawing Sheets

(58) Field of Classification Search
CPC .... A61K 45/06; A61K 31/343; A61K 31/365;
A61P 35/02; A61P 35/00; Y02A 50/30
See application file for complete search history.

(56) References Cited

FOREIGN PATENT DOCUMENTS

| | | | |
|---|---|---|---|
| CN | 111303100 | A | 6/2020 |
| WO | 2011131103 | A1 | 10/2011 |
| WO | 2014056410 | A1 | 4/2014 |
| WO | 2015006893 | A1 | 1/2015 |
| WO | 2017128163 | A1 | 8/2017 |

\* cited by examiner

HYDRATE OF DIMETHYLAMINOMICHELIOLIDE FUMARATE AND PREPARATION METHOD THEREFOR AND USE THEREOF

TECHNICAL FIELD

The present disclosure belongs to the technical field of drug crystallization, and particularly relates to a hydrate of dimethylaminomicheliolide fumarate, a preparation method therefor and use thereof.

BACKGROUND

Parthenolide is a main active ingredient extracted from Asteraceae plant herbs feverfew and tansy, and is a naturally occurring sesquiterpene lactone. Traditionally, feverfew is mainly used to treat diseases such as fever, rheumatoid arthritis, migraine and toothache. In recent years, studies in China and other countries have found that parthenolide also has an anti-tumor effect but is unstable in property under acidic or basic conditions.

In order to improve its stability, the compound parthenolide is modified to obtain micheliolide (MCL), a guaiane-type sesquiterpene lactone. It has been reported in the relevant literature(s) and patent(s) that micheliolide has an effect in treating cancer diseases but has poor solubility in water. In order to improve the solubility in water and the biological activity, with triethylamine as a catalyst, a reaction is performed through heating in a methanol solvent to obtain a micheliolide derivative, i.e., dimethylaminomicheliolide (DMAMCL) with a molecular formula of $C_{17}H_{27}NO_3$ and a structural formula below. DMAMCL has improved solubility in water to a certain degree relative to MCL but is unstable as it will degrade after long-term storage. In order to further improve its solubility in water and stability, it is often prepared in the form of a salt. The inventors have discovered dimethylaminomicheliolide fumarate prepared from a parthenolide derivative. Meanwhile, the patent WO2011/131103A1 discloses a preparation method for micheliolide derivatives or salts thereof or pharmaceutical compositions thereof including dimethylaminomicheliolide fumarate and their use in preparing a medicament for treating cancer.

Dimethylaminomicheliolide fumarate has a molecular formula of $C_{21}H_{31}NO_7$ and a relative molecular mass of 409. It is a colorless and odorless white crystalline powder. It is soluble in water, methanol, ethanol, tetrahydrofuran, 1,4-dioxane, acetone, acetonitrile and isopropyl acetate, and is almost insoluble in cyclohexane, n-hexane, n-heptane, dichloromethane, isopropyl ether and toluene. The chemical structural formula is as follows:

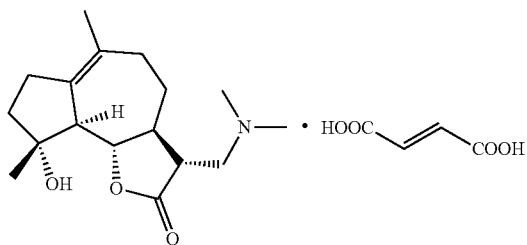

Polymorphism refers to the existence of a substance in different crystal structures arising from different molecular arrangements or conformations. It occurs among 80% of commercially available drugs according to statistics. Different crystalline forms of a drug are different in physicochemical properties such as color, solubility, melting point, density, hardness and crystal morphology, thereby leading to differences in qualities such as stability, dissolution rate and bioavailability of the drug and thus affecting subsequent processing and treatment, as well as the therapeutic effects and safety of the drug to some extent. In the process of drug quality control and design of new pharmaceutical dosage forms, research on drug polymorphism has become an indispensable important part.

Chinese patent CN103724307B discloses dimethylaminomicheliolide fumarate in a crystalline form A and a preparation method therefor. The crystalline form A is characterized by XRPD in the patent, having characteristic peaks at 2θ of 7.10°, 7.58°, 11.72°, 12.26°, 13.30°, 14.24°, 15.70°, 16.38°, 17.04°, 19.02°, 19.86°, 20.14°, 20.66°, 21.20°, 21.78°, 22.64°, 23.58°, 23.8°, 24.48°, 25.08°, 26.24°, 27.08°, 27.60°, 28.40°, 28.94°, 34.48°, 34.82°, 36.12°, 38.72° and 45°. The crystalline form A is prepared by recrystallization from an ethyl acetate solvent. In this method, the product is prepared by natural cooling. However, as the recrystallization process is controlled by both of thermodynamics and dynamics, the conditions for the recrystallization by-natural cooling are greatly affected by changes in the environment, and the cooling rate is difficult to control, leading to a small particle size of the product, the primary particle size being 35.8 μm, a low bulk density of mere 0.270 g/mL, an angle of repose of 62°, poor fluidity and big differences in quality between crystal products of different batches. Meanwhile, the crystalline form A has poor stability as it is prone to transformation, and there is electrostatic action in the solid powder, leading to clouds of dust in the production process and thus causing many problems in processing and treatment at a later stage.

SUMMARY

In order to solve the above problems, the present disclosure provides a hydrate of dimethylaminomicheliolide fumarate, a preparation method therefor and use thereof. A crystal product of the hydrate of dimethylaminomicheliolide fumarate with high crystallinity, high bulk density, good fluidity, large particle size, smooth and clean crystal surfaces without agglomeration, and good stability is prepared by reactive crystallization. The preparation method is simple and features high product yield and good reproducibility, favoring large-scale production.

The present disclosure provides a hydrate of dimethylaminomicheliolide fumarate, wherein the hydrate is in a crystalline form D, the molar ratio of dimethylaminomicheliolide fumarate to water is 1:1, and the hydrate has a molecular formula of $C_{17}H_{27}NO_3 \cdot C_4H_4O_4 \cdot H_2O$; as shown in thermogravimetric analysis/differential scanning calorimetry analysis patterns, the thermogravimetric analysis shows a weight loss of 3.97%-4.22% before decomposition; the differential scanning calorimetry pattern shows a dehydration endothermic peak at 75±5° C. and a characteristic melting peak at 148±5° C.

The present disclosure provides a hydrate of dimethylaminomicheliolide fumarate, wherein the hydrate has characteristic peaks at 2θ angles of 7.8±0.2°, 11.1±0.2°, 11.4±0.2°, 12.6±0.2°, 12.9±0.2°, 14.4±0.2°, 15.3±0.2°, 17.0±0.2°, 18.7±0.2°, 19.7±0.2°, 20.6±0.2°, 21.0±0.2°, 22.5±0.2°, 23.7±0.2°, 24.3±0.2°, 25.5±0.2° and 26.2±0.2° in an X-ray powder diffraction pattern using Cu-Kα radiation, wherein the peak at 7.8±0.2° is an initial peak; the characteristic peak at 20.6±0.2° has a relative intensity of 100%; the crystalline form D is in an orthorhombic crystal system and has a space group of $P2_12_12_1$, a cell parameter of a=8.8346(18) Å, b=14.796(3) Å, c=16.385(3) Å, α=90°, β=90°, and γ=90°; and a cell volume of 2141.8(8) Å³.

The present disclosure provides a hydrate of dimethylaminomicheliolide fumarate, wherein the hydrate also has characteristic peaks at 2θ angles of 10.5±0.2°, 11.7±0.2°, 12.0±0.2°, 15.6±0.2°, 15.9±0.2°, 16.2±0.2°, 21.3±0.2°, 22.1±0.2°, 23.0±0.2°, 26.4±0.2°, 27.2±0.2°, 28.2±0.2°, 28.6±0.2°, 29.3±0.2°, 30.4±0.2° and 31.1±0.2° in an X-ray powder diffraction pattern using Cu-Kα radiation. The present disclosure also provides a preparation method for a hydrate of dimethylaminomicheliolide fumarate, which can be implemented by reactive crystallization: under the action of stirring, adding dimethylaminomicheliolide and fumaric acid to a mixed solvent system of a solvent S1 and a solvent S2 at a constant temperature of 30° C.-70° C., with the mass ratio of the solvent S2 to the solvent S1 being (0-3):1 and the molar ratio of dimethylaminomicheliolide to fumaric acid being (1-1.6):1; after 5-10 h of reaction, filtering the reaction mixture and drying the residue at 25° C.-45° C. under normal pressure for 6 h-10 h to obtain dimethylaminomicheliolide fumarate in a crystalline form D.

The solvent S1 is a mixed solvent of water and any one of acetone, tetrahydrofuran, 1,4-dioxane, acetonitrile and methyl isobutyl ketone.

The solvent S2 is a mixed solvent of ester and ether solvents.

The ester solvent is selected from any one or two of methyl acetate, ethyl acetate, hexyl acetate and isopropyl acetate.

The ether solvent is selected from any one or two of diethyl ether, methyl ethyl ether, methyl tert-butyl ether, dipropyl ether, dibutyl ether, ethylene glycol dimethyl ether, ethylene glycol monomethyl ether, 1,4-dioxane, tetrahydrofuran and 2-methyl tetrahydrofuran.

The solvent S1 is a mixed solvent of water and any one of acetone, tetrahydrofuran, 1,4-dioxane, acetonitrile and methyl isobutyl ketone.

The mass ratio of the ester solvent to the ether solvent in the solvent S2 is (1-3):1.

The mass ratio of the solid starting material dimethylaminomicheliolide to S1 is 1:(6-10).

The crystal habit of the hydrate of dimethylaminomicheliolide fumarate is studied in the present disclosure, and a scanning electron micrograph thereof is shown in FIG. 3. —The crystal has a regular block crystal habit, and the surface of the particle is smooth without agglomeration, meanwhile, the crystal has a large average particle size that can reach 300 μm, a bulk density of 0.65 g/mL, and an angle of repose of 32°. The product features high bulk density and good fluidity. In comparison, the crystalline form A prepared using the natural cooling recrystallization method disclosed in patent CN103724307B has a primary particle size of 35.8 μm, a bulk density of mere 0.270 g/mL and an angle of repose of 62°, and a scanning electron micrograph thereof is shown in FIG. 4. The dimethylaminomicheliolide fumarate product in the crystalline form D provided in the present disclosure has a significantly improved particle size, solving the problems of the low bulk density and poor fluidity of the product in the crystalline form A.

The stability of the hydrate of dimethylaminomicheliolide fumarate is investigated in the present disclosure. The anhydrous crystal compound product is uniformly distributed in an open Petri dish. The temperature is controlled at 45° C., the humidity is 75%, and the sample thickness is less than 5 mm. The Petri dish is hermetically placed in a drier for 30 days. Then the samples placed for 7, 14 and 30 days were examined by XRD and compared with the results on day 0. The specific pattern is shown in FIG. 5. The results show no significant change in the XRD pattern. Meanwhile, the samples at days 7, 14 and 30 are subjected to purity analysis. By comparison with the results of the purity detection at day 0, a change of mere 0.015% is observed in the purity of the sample at day 7, a change of mere 0.027% is observed in the purity of the sample at day 14, and a change of mere 0.046% is observed in the purity of the sample at day 30, suggesting no significant change in the purity of the sample. By combining the XRD patterns and the results of the purity analysis, the hydrate of dimethylaminomicheliolide fumarate is shown to have good stability.

The hydrate of dimethylaminomicheliolide fumarate provided in the present disclosure can be used to prepare a solventless compound of dimethylaminomicheliolide fumarate in a crystalline form B. The preparation method for the crystalline form B comprises: heating the hydrate of dimethylaminomicheliolide fumarate at a constant temperature of 80° C.-120° C. for 10 min-30 min to obtain the solventless compound of dimethylaminomicheliolide fumarate in a crystalline form B, whose X-ray powder diffraction pattern is shown in FIG. 6, showing characteristic peaks at 2θ angles of 8.1±0.2°, 10.7±0.2°, 11.5±0.2°, 11.9±0.2°, 13.0±0.2°, 13.3±0.2°, 14.7±0.2°, 15.9±0.2°, 16.1±0.2°, 16.7±0.2°, 17.1±0.2°, 19.0±0.2°, 19.9±0.2°, 20.3±0.2°, 21.2±0.2°, 21.5±0.2°, 22.1±0.2°, 23.0±0.2°, 23.5±0.2°, 24.4±0.2°, 26.0±0.2°, 26.6±0.2°, 26.9±0.2°, 27.4±0.2°, 27.9±0.2°, 28.6±0.2°, 29.4±0.2°, 30.2±0.2° and 31.0±0.2°. The scanning electron micrograph is similar to that in FIG. 5, indicating that the crystal habit is consistent with the hydrate and the particle size is large.

The hydrate of dimethylaminomicheliolide fumarate of the present disclosure also provides a pharmaceutical composition, which comprises a pharmaceutically acceptable auxiliary material and may also comprise one, two or more other pharmacologically active ingredients other than the hydrate of dimethylaminomicheliolide fumarate.

The pharmaceutically acceptable auxiliary material includes, but is not limited to, other non-pharmacologically active ingredients other than active ingredients such as dimethylaminomicheliolide fumarate in a crystalline form, e.g., non-pharmacologically active ingredients that may be used for the pharmaceutical composition of the present disclosure, including carriers or excipients such as fillers, glidants, lubricants, binders, stabilizers and/or other auxiliary materials.

The fillers include, but are not limited to, at least one of maize starch, glucose, mannitol, sorbitol, silica, microcrystalline cellulose, sodium carboxymethyl starch, composite starch and pregelatinized starch.

The flow aids include, but are not limited to, at least one of silica, hydrated silica, light anhydrous silicic acid, dry aluminum hydroxide gel, aluminum silicate and magnesium silicate.

The lubricants include, but are not limited to, at least one of wheat starch, rice starch, maize starch, stearic acid, calcium stearate, magnesium stearate, hydrated silica, light anhydrous silicic acid, synthetic aluminum silicate, dry aluminum hydroxide gel, talc, magnesium aluminometasilicate, dicalcium phosphate, anhydrous dicalcium phosphate, sucrose fatty acid esters, paraffins, hydrogenated vegetable oil and polyethylene glycol.

The pharmaceutical composition according to the present disclosure is used for preparing a pharmaceutical preparation, wherein the pharmaceutical preparation includes the pharmaceutical composition in a tablet, capsule or granule dosage form. The pharmaceutical preparation is more preferably a capsule.

The present disclosure also provides use of the hydrate of dimethylaminomicheliolide fumarate or the pharmaceutical composition in preparing a medicament for the treatment or prevention of a disease or condition, wherein the disease or condition is preferably cancer selected from leukemia, breast cancer, prostate cancer, nasopharyngeal cancer, large intestine cancer, lung cancer, liver cancer, esophageal cancer, gastric cancer, intestinal cancer, renal cancer, oral cancer, Hodgkin's lymphoma, pancreatic cancer, colorectal cancer, cervical cancer, non-Hodgkin's lymphoma, glioma, melanoma, bladder cancer, ovarian cancer, thyroid cancer and Kaposi's sarcoma.

Beneficial Effects

The hydrate of the present disclosure has good fluidity and is more suitable for being prepared as a medicament at a later stage. It is well known that the fluidity of an active ingredient per se is generally hard to meet the filling conditions of capsules or microcapsules, and auxiliary materials such as pregelatinized starch, silica and magnesium stearate are required to meet the requirements for fluidity by the filling conditions so as to achieve the desired quality of dosage forms and production efficiency. Taking the specification of 100 mg capsules as an example, if other forms such as crystalline form A are used as active ingredients, the weight of capsule contents reaches about 310 mg after auxiliary materials are added, and thus the largest 0 # capsule shell must be used, and larger specification such as capsules containing 200 mg of active ingredients cannot be prepared. For this reason, patients would have to achieve high dose administration by increasing the number of capsules taken or the frequency of administrations, which would significantly reduce patient compliance. However, the inventors have found that an angle of repose of 32° can be achieved due to the excellent fluidity of the hydrate of dimethylaminomicheliolide fumarate in the crystalline form D even without adding auxiliary materials. For this reason, the required fluidity for the filling conditions of capsules or microcapsules can be achieved with significantly reduced amounts of auxiliary materials and even without adding any auxiliary material. Moreover, the reduction in the amounts of auxiliary materials makes it possible to produce capsules of high-dose specifications, significantly improving patient compliance.

Furthermore, due to the fact that the hydrate of dimethylaminomicheliolide fumarate in the crystalline form D can significantly or even completely reduce the addition of auxiliary materials, and that a large amount of auxiliary materials are required for the crystalline form A to achieve the same fluidity as the crystalline form D, resulting in poor stability, the hydrate in the crystalline form D improves the stability of the preparation.

In addition, the preparation method for the hydrate of dimethylaminomicheliolide fumarate in the crystalline form D is simple and features high product yield and good reproducibility, and the resulting product has high crystallinity, smooth and clean particle surfaces without agglomeration, no static electricity between particles and high bulk density, favoring large-scale production.

DETAILED DESCRIPTION

The above description of the present disclosure will be further explained in detail through specific embodiments in the form of examples. However, it should not be interpreted as limiting the scope of the above subject matter of the present disclosure to the examples below. All techniques implemented based on the above description of the present disclosure fall within the scope of the present disclosure.

Example 1

Preparation of Hydrate of Dimethylaminomicheliolide Fumarate

Figure 1:
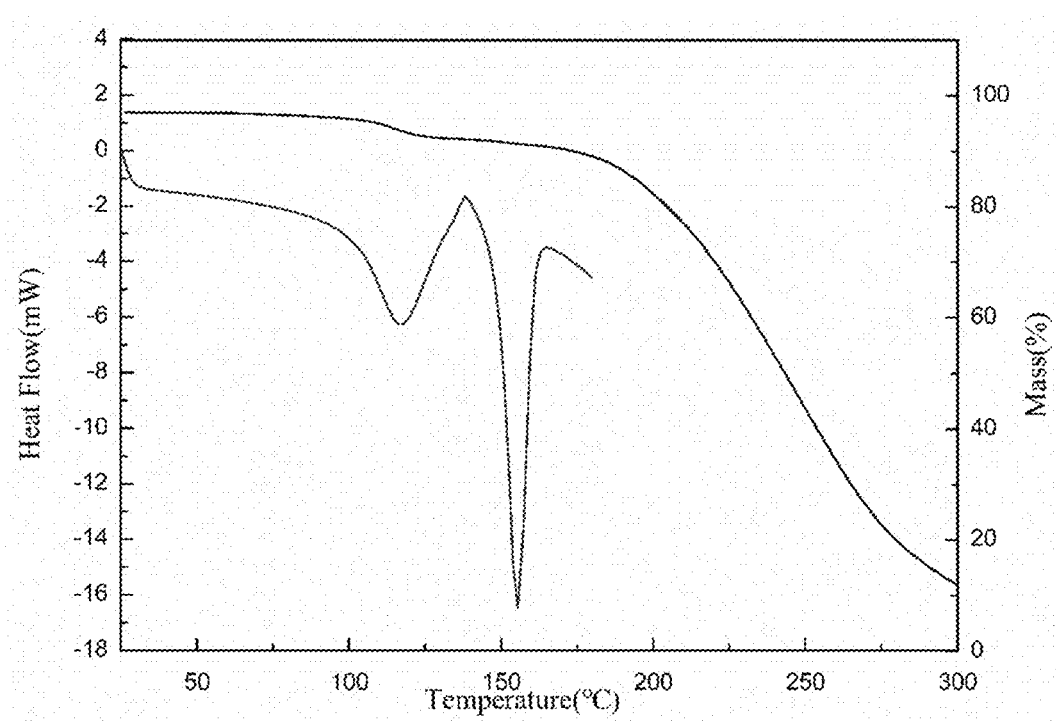
FIG. 1 shows a pattern of thermogravimetric analysis/differential scanning calorimetry of the hydrate of dimethylaminomicheliolide fumarate of the present disclosure.
Figure 2:
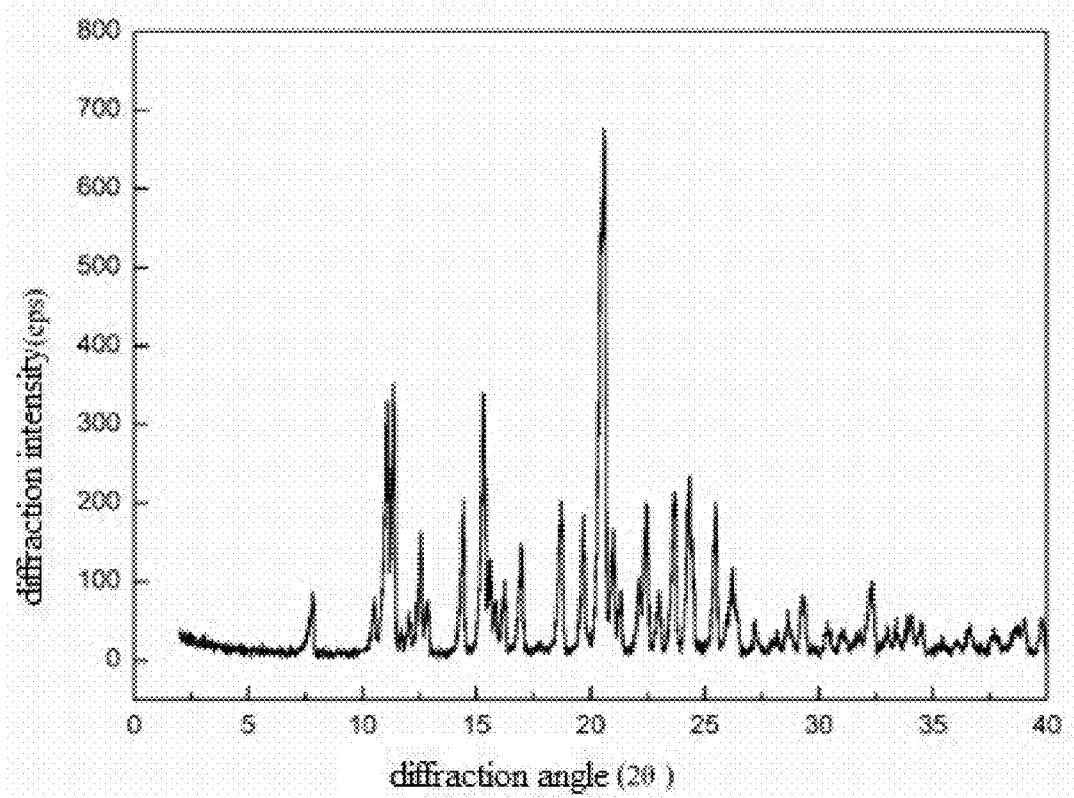
FIG. 2 shows a pattern of X-ray diffraction of the hydrate of dimethylaminomicheliolide fumarate of the present disclosure.
Figure 3:
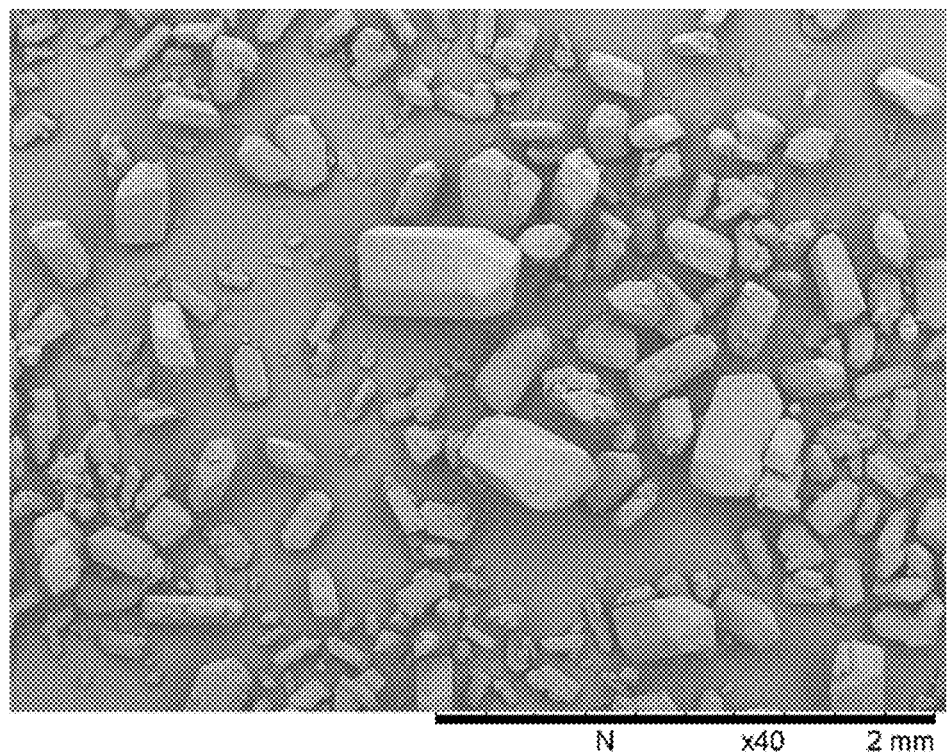
FIG. 3 shows a scanning electron micrograph of the hydrate of dimethylaminomicheliolide fumarate of the present disclosure (at a magnification of 40).
Figure 4:
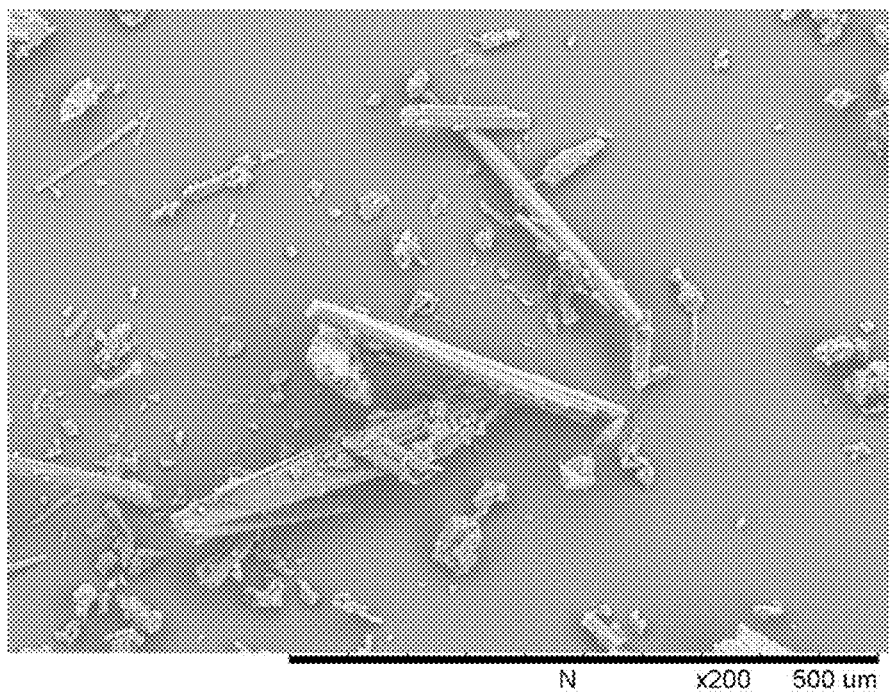
FIG. 4 shows a scanning electron micrograph of a product in the crystalline form A prepared according to the method disclosed in patent CN103724307B (at a magnification of 200).

Under the action of stirring, 0.293 g of dimethylaminomicheliolide and 0.116 g of fumaric acid were added to a mixed solvent system of a solvent S1 and a solvent S2 at a constant temperature of 30° C., with the mass of the solvent S1 being the same as that of the solvent S2, wherein the solvent S1 consisted of 1.598 g of acetone solvent and 0.16 g of water, and the solvent S2 consisted of 0.879 g of ethyl acetate and 0.879 g of diethyl ether. After 5 h of reaction, the reaction mixture was filtered, and the residue was dried at 25° C. under normal pressure for 6 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 4.22% before decomposition, and the differential scanning calorimetry analysis shows a dehydration endothermic peak at 75° C. and a characteristic melting peak at 148° C. The X-ray powder diffraction pattern of the product is consistent with FIG. 2, showing characteristic peaks at diffraction angles 2θ of 7.8°, 11.1°, 11.4°, 12.6°, 12.9°, 14.4°, 15.3°, 17.0°, 18.7°, 19.7°, 20.6°, 21.0°, 22.5°, 23.7°, 24.3°, 25.5° and 26.2°, wherein the peak at 7.8° is an initial peak, and the characteristic peak at 20.6° has a relative intensity of 100%. The X-ray powder diffraction pattern of the product also shows characteristic peaks at 2θ angles of 10.5±0.2°, 11.7±0.2°, 12.0±0.2°, 15.6±0.2°, 15.9±0.2°, 16.2±0.2°, 21.3±0.2°, 22.1±0.2°, 23.0±0.2°, 26.4±0.2°, 27.2±0.2°, 28.2±0.2°, 28.6±0.2°, 29.3±0.2°, 30.4±0.2° and 31.1±0.2°. The SEM image of the crystal morphology is consistent with FIG. 4, indicating bulk crystals with a large average particle size that may reach 300 μm, a tested bulk density of 0.646 g/mL and an angle of repose of 32.5°.

Example 2

Preparation of Hydrate of Dimethylaminomicheliolide Fumarate

Under the action of stirring, 1.758 g of dimethylaminomicheliolide and 0.58 g of fumaric acid were added to a mixed solvent system of a solvent S1 and a solvent S2 at a constant temperature of 50° C., with the mass of the solvent S2 being 2 times that of the solvent S1, wherein the solvent S1 consisted of 12.306 g of tetrahydrofuran solvent and 1.758 g of water, and the solvent S2 consisted of 21.096 g of isopropyl acetate and 7.032 g of methyl tert-butyl ether. After 8 h of reaction, the reaction mixture was filtered, and the residue was dried at 30° C. under normal pressure for 10 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 4.20% before decomposition, and the differential scanning calorimetry analysis shows a dehydration endothermic peak at 78° C. and a characteristic melting peak at 150° C. The X-ray powder diffraction pattern of the product is consistent with FIG. 2, showing characteristic peaks at diffraction angles 2θ of 8.0°, 11.2°, 11.5°, 12.7°, 12.9°, 14.5°, 15.4°, 17.1°, 18.8°, 19.8°, 20.6°, 21.1°, 22.5°, 23.7°, 24.5°, 25.6° and 26.3°, wherein the peak at 7.8° is an initial peak, and the characteristic peak at 20.6° has a relative intensity of 100%. The X-ray powder diffraction pattern of the product also shows characteristic peaks at 2θ angles of 10.6°, 11.8°, 12.2°, 15.1°, 15.7°, 16.0°, 21.4°, 22.0°, 22.3°, 23.1°, 27.3°, 28.2°, 28.7°, 29.4°, 30.5°, 30.6° and 31.3°. The SEM image of the crystal morphology is consistent with FIG. 4, indicating bulk crystals with a large average particle size that may reach 300 μm, a tested bulk density of 0.655 g/mL and an angle of repose of 32°.

Example 3

Preparation of Hydrate of Dimethylaminomicheliolide Fumarate

Under the action of stirring, 4.688 g of dimethylaminomicheliolide and 1.16 g of fumaric acid were added to a mixed solvent system of a solvent S1 and a solvent S2 at a constant temperature of 70° C., with the mass of the solvent S2 being 3 times that of the solvent S1, wherein the solvent S1 consisted of 39 g of 1,4-dioxane solvent and 7.88 g of water, and the solvent S2 consisted of 93.76 g of methyl acetate and 46.88 g of methyl ethyl ether. After 10 h of reaction, the reaction mixture was filtered, and the residue was dried at 45° C. under normal pressure for 8 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 3.97% before decomposition, and the differential scanning calorimetry analysis shows a dehydration endothermic peak at 75° C. and a characteristic melting peak at 145° C. The X-ray powder diffraction pattern of the product is consistent with FIG. 2, showing characteristic peaks at diffraction angles 2θ of 7.8°, 11.0°, 11.4°, 12.5°, 12.8°, 14.4°, 15.3°, 17.0°, 18.7°, 19.7°, 20.6°, 21.0°, 22.4°, 23.7°, 24.3°, 25.4° and 26.2°, wherein the peak at 7.8° is an initial peak, and the characteristic peak at 20.6° has a relative intensity of 100%. The X-ray powder diffraction pattern of the product also shows characteristic peaks at 2θ angles of 10.5°, 11.7°, 12.0°, 15.6°, 15.9°, 16.2°, 21.3°, 22.2°, 22.9°, 26.4°, 27.3°, 28.2°, 28.6°, 29.3°, 30.4° and 31.1°. The SEM image of the crystal morphology is consistent with FIG. 4, indicating bulk crystals with a large average particle size that may reach 300 μm, a tested bulk density of 0.65 g/mL and an angle of repose of 32°.

Example 4

Preparation of Hydrate of Dimethylaminomicheliolide Fumarate

Under the action of stirring, 4.102 g of dimethylaminomicheliolide and 1.16 g of fumaric acid were added to a mixed solvent system of a solvent S1 and a solvent S2 at a constant temperature of 60° C., with the mass of the solvent S2 being 3 times that of the solvent S1, wherein the solvent S1 consisted of 35.8925 g of acetonitrile solvent and 5.1275 g of water, and the solvent S2 consisted of 87.9 g of hexyl acetate and 35.16 g of ethylene glycol dimethyl ether. After 10 h of reaction, the reaction mixture was filtered, and the residue was dried at 45° C. under normal pressure for 9 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 4.10% before decomposition, and the differential scanning calorimetry analysis shows a dehydration endothermic peak at 80° C. and a characteristic melting peak at 150° C. The X-ray powder diffraction pattern of the product is consistent with FIG. 2, showing characteristic peaks at diffraction angles 2θ of 7.8°, 11.1°, 11.4°, 12.6°, 12.9°, 14.4°, 15.4°, 17.0°, 18.8°, 19.8°, 20.6°, 21.0°, 22.5°, 23.7°, 24.4°, 25.5° and 26.2°, wherein the peak at 7.8° is an initial peak, and the characteristic peak at 20.6° has a relative intensity of 100%. The X-ray powder diffraction pattern of the product also shows characteristic peaks at 2θ angles of 10.6°, 11.8°, 12.1°, 15.9°, 16.3°, 21.4°, 22.2°, 23.0°, 26.5°, 27.3°, 28.7°, 29.3°, 30.4° and 31.1°. The SEM image of the crystal morphology is consistent with FIG. 4, indicating bulk crystals with a large average particle size that may reach 300 μm, a tested bulk density of 0.659 g/mL and an angle of repose of 32.2°.

Example 5

Preparation of Hydrate of Dimethylaminomicheliolide Fumarate

Under the action of stirring, 0.293 g of dimethylaminomicheliolide and 0.116 g of fumaric acid were added to a mixed solvent system of a solvent S1 and a solvent S2 at a constant temperature of 30° C., with the mass of the solvent S1 being the same as that of the solvent S2, wherein the solvent S1 consisted of 1.598 g of acetonitrile solvent and 0.16 g of water, and the solvent S2 consisted of 0.879 g of isopropyl acetate and 0.879 g of ethylene glycol monomethyl ether. After 5 h of reaction, the reaction mixture was filtered, and the residue was dried at 25° C. under normal pressure for 6 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 4.22% before decomposition, and the differential scanning calorimetry analysis shows a dehydration endothermic peak at 75° C. and a characteristic melting peak at 148° C. The X-ray powder diffraction pattern of the product is consistent with FIG. 2, showing characteristic peaks at diffraction angles 2θ of 7.8°, 11.1°, 11.4°, 12.6°, 12.9°, 14.4°, 15.3°, 17.0°, 18.7°, 19.7°, 20.6°, 21.0°, 22.5°, 23.7°, 24.3°, 25.5° and 26.2°, wherein the peak at 7.8° is an initial peak, and the characteristic peak at 20.6° has a relative intensity of 100%. The X-ray powder diffraction pattern of the product also shows characteristic peaks at 2θ angles of 10.5±0.2°, 11.7±0.2°, 12.0±0.2°, 15.6±0.2°, 15.9±0.2°, 16.2±0.2°, 21.3±0.2°, 22.1±0.2°, 23.0±0.2°, 26.4±0.2°, 27.2±0.2°, 28.2±0.2°, 28.6±0.2°, 29.3±0.2°, 30.4±0.2° and 31.1±0.2°. The SEM image of the crystal morphology is consistent with FIG. 4, indicating bulk crystals with a large average particle size that may reach 300 μm, a tested bulk density of 0.645 g/mL and an angle of repose of 32°.

Example 6

Preparation of Hydrate of Dimethylaminomicheliolide Fumarate

Under the action of stirring, 4.688 g of dimethylaminomicheliolide and 1.16 g of fumaric acid were added to a mixed solvent system of a solvent S1 and a solvent S2 at a constant temperature of 70° C., with the mass of the solvent S2 being 3 times that of the solvent S1, wherein the solvent S1 consisted of 39 g of methyl isobutyl ketone solvent and 7.88 g of water, and the solvent S2 consisted of 46.88 g of methyl acetate, 46.88 g of isopropyl acetate, 23.44 g of tetrahydrofuran and 23.44 g of dibutyl ether. After 10 h of reaction, the reaction mixture was filtered, and the residue was dried at 45° C. under normal pressure for 8 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 3.97% before decomposition, and the differential scanning calorimetry analysis shows a dehydration endothermic peak at 75° C. and a characteristic melting peak at 145° C. The X-ray powder diffraction pattern of the product is consistent with FIG. 2, showing characteristic peaks at diffraction angles 2θ of 7.8°, 11.0°, 11.4°, 12.5°, 12.8°, 14.4°, 15.3°, 17.0°, 18.7°, 19.7°, 20.6°, 21.0°, 22.4°, 23.7°, 24.3°, 25.4° and 26.2°, wherein the peak at 7.8° is an initial peak, and the characteristic peak at 20.6° has a relative intensity of 100%. The X-ray powder diffraction pattern of the product also shows characteristic peaks at 2θ angles of 10.5°, 11.7°, 12.0°, 15.6°, 15.9°, 16.2°, 21.3°, 22.2°, 22.9°, 26.4°, 27.3°, 28.2°, 28.6°, 29.3°, 30.4° and 31.1°. The SEM image of the crystal morphology is consistent with FIG. 4, indicating bulk crystals with a large average particle size that may reach 300 μm, a tested bulk density of 0.65 g/mL and an angle of repose of 32.3°.

Example 7

Preparation of Hydrate of Dimethylaminomicheliolide Fumarate

Under the action of stirring, 1.758 g of dimethylaminomicheliolide and 0.58 g of fumaric acid were added to a mixed solvent system of a solvent S1 and a solvent S2 at a constant temperature of 50° C., with the mass of the solvent S2 being 2 times that of the solvent S1, wherein the solvent S1 consisted of 12.306 g of methyl isobutyl ketone solvent and 1.758 g of water, and the solvent S2 consisted of 21.096 g of methyl acetate and 7.032 g of 2-methyl tetrahydrofuran. After 9 h of reaction, the reaction mixture was filtered, and the residue was dried at 30° C. under normal pressure for 10 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 4.20% before decomposition, and the differential scanning calorimetry analysis shows a dehydration endothermic peak at 78° C. and a characteristic melting peak at 150° C. The X-ray powder diffraction pattern of the product is consistent with FIG. 2, showing characteristic peaks at diffraction angles 2θ of 8.0°, 11.2°, 11.5°, 12.7°, 12.9°, 14.5°, 15.4°, 17.1°, 18.8°, 19.8°, 20.6°, 21.1°, 22.5°, 23.7°, 24.5°, 25.6° and 26.3°, wherein the peak at 7.8° is an initial peak, and the characteristic peak at 20.6° has a relative intensity of 100%. The X-ray powder diffraction pattern of the product also shows characteristic peaks at 2θ angles of 10.6°, 11.8°, 12.2°, 15.1°, 15.7°, 16.0°, 21.4°, 22.0°, 22.3°, 23.1°, 27.3°, 28.2°, 28.7°, 29.4°, 30.5°, 30.6° and 31.3°. The SEM image of the crystal morphology is consistent with FIG. 4, indicating bulk crystals with a large average particle size that may reach 300 μm, a tested bulk density of 0.65 g/mL and an angle of repose of 32°.

Example 8

Preparation of Hydrate of Dimethylaminomicheliolide Fumarate

Under the action of stirring, 4.102 g of dimethylaminomicheliolide and 1.16 g of fumaric acid were added to a mixed solvent system of a solvent S1 and a solvent S2 at a constant temperature of 60° C., with the mass of the solvent S2 being 3 times that of the solvent S1, wherein the solvent S1 consisted of 35.8925 g of tetrahydrofuran solvent and 5.1275 g of water, and the solvent S2 consisted of 87.9 g of methyl acetate and 35.16 g of 1,4-dioxane. After 10 h of reaction, the reaction mixture was filtered, and the residue was dried at 45° C. under normal pressure for 9 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 4.10% before decomposition, and the differential scanning calorimetry analysis shows a dehydration endothermic peak at 80° C. and a characteristic melting peak at 150° C. The X-ray powder diffraction pattern of the product is consistent with FIG. 2, showing characteristic peaks at diffraction angles 2θ of 7.8°, 11.1°, 11.4°, 12.6°, 12.9°, 14.4°, 15.3°, 17.0°, 18.7°, 19.7°, 20.6°, 21.0°, 22.5°, 23.7°, 24.3°, 25.5° and 26.2°, wherein the peak at 7.8° is an initial peak, and the characteristic peak at 20.6° has a relative intensity of 100%. The X-ray powder diffraction pattern of the product also shows characteristic peaks at 2θ angles of 10.5±0.2°, 11.7±0.2°, 12.0±0.2°, 15.6±0.2°, 15.9±0.2°, 16.2±0.2°, 21.3±0.2°, 22.1±0.2°, 23.0±0.2°, 26.4±0.2°, 27.2±0.2°, 28.2±0.2°, 28.6±0.2°, 29.3±0.2°, 30.4±0.2° and 31.1±0.2°. The SEM image of the crystal morphology is consistent with FIG. 4, indicating bulk crystals with a large average particle size that may reach 300 μm, a tested bulk density of 0.654 g/mL and an angle of repose of 32.1°.

Example 9

Preparation of Hydrate of Dimethylaminomicheliolide Fumarate

Under the action of stirring, 0.293 g of dimethylaminomicheliolide and 0.116 g of fumaric acid were added to a mixed solvent system of a solvent S1 and a solvent S2 at a constant temperature of 30° C., with the mass of the solvent S1 being the same as that of the solvent S2, wherein the solvent S1 consisted of 1.598 g of acetone solvent and 0.16 g of water, and the solvent S2 consisted of 0.879 g of isopropyl acetate and 0.879 g of dipropyl ether. After 7 h of reaction, the reaction mixture was filtered, and the residue was dried at 25° C. under normal pressure for 6 h to obtain a product of dimethylaminomicheliolide fumarate in the crystalline form D. The thermogravimetric analysis/differential scanning calorimetry of the product is consistent with FIG. 1. The thermogravimetric analysis shows a weight loss of 4.22% before decomposition, and the differential scanning calorimetry analysis shows a dehydration endothermic peak at 75° C. and a characteristic melting peak at 148° C. The X-ray powder diffraction pattern of the product is consistent with FIG. 2, showing characteristic peaks at diffraction angles 2θ of 7.8°, 11.0°, 11.4°, 12.5°, 12.8°, 14.4°, 15.3°, 17.0°, 18.7°, 19.7°, 20.6°, 21.0°, 22.4°, 23.7°, 24.3°, 25.4° and 26.2°, wherein the peak at 7.8° is an initial peak, and the characteristic peak at 20.6° has a relative intensity of 100%. The X-ray powder diffraction pattern of the product also shows characteristic peaks at 2θ angles of 10.5°, 11.7°, 12.0°, 15.6°, 15.9°, 16.2°, 21.3°, 22.2°, 22.9°, 26.4°, 27.3°, 28.2°, 28.6°, 29.3°, 30.4° and 31.1°. The SEM image of the crystal morphology is consistent with FIG. 4, indicating bulk crystals with a large average particle size that may reach 300 μm, a tested bulk density of 0.645 g/mL and an angle of repose of 32.3°.

Example 10

Figure 5:
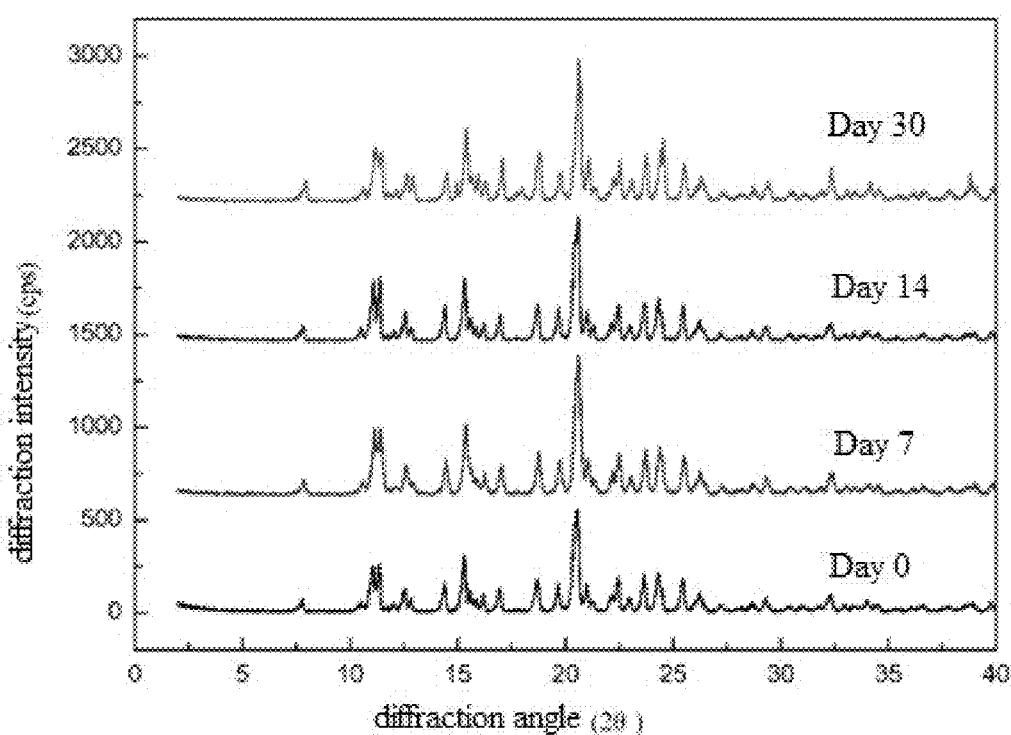
FIG. 5 shows comparisons of stability test patterns of the hydrate of dimethylaminomicheliolide fumarate of the present disclosure, wherein from bottom to top are sequentially placed the XRD patterns of samples at days 0, 7, 14 and 30.
Figure 6:
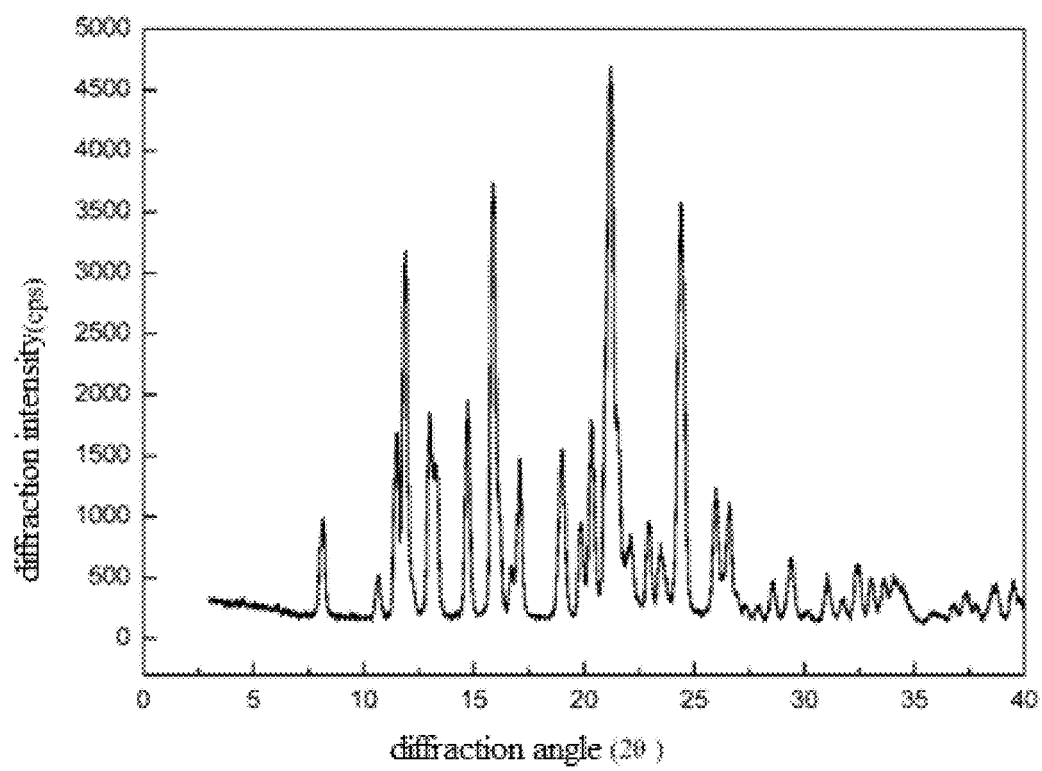
FIG. 6 shows an X-ray diffraction pattern of the solventless compound of dimethylaminomicheliolide fumarate in the crystalline form B of the present disclosure.

Preparation of Solventless Compound of Dimethylaminomicheliolide Fumarate in Crystalline Form B 0.1 g of the product of Example 1 was weighed into a variable-temperature X-ray diffractometer, and heated at a constant temperature of 80° C. for 30 min. A sample was taken for XRD analysis, and the resulting pattern is consistent with FIG. 6, indicating a solventless compound of dimethylaminomicheliolide fumarate in the crystalline form B. The scanning electron micrograph of the solid shows a morphology consistent with that shown in FIG. 5, indicating that the block-shaped crystal habit was retained.

Example 11

Preparation of Solventless Compound of Dimethylaminomicheliolide Fumarate in Crystalline Form B 0.15 g of the product of Example 3 was weighed into a variable-temperature X-ray diffractometer, and heated at a constant temperature of 120° C. for 10 min. A sample was taken for XRD analysis, and the resulting pattern is consistent with FIG. 6, indicating a solventless compound of dimethylaminomicheliolide fumarate in the crystalline form B. The scanning electron micrograph of the solid shows a morphology consistent with that shown in FIG. 5, indicating that the block-shaped crystal habit was retained.

Example 12

Preparation of Solventless Compound of Dimethylaminomicheliolide Fumarate in Crystalline Form B 0.1 g of the product of Example 4 was weighed into a variable-temperature X-ray diffractometer, and heated at a constant temperature of 100° C. for 20 min. A sample was taken for XRD analysis, and the resulting pattern is consistent with FIG. 6, indicating a solventless compound of dimethylaminomicheliolide fumarate in the crystalline form B. The scanning electron micrograph of the solid shows a morphology consistent with that shown in FIG. 5, indicating that the block-shaped crystal habit was retained.

Example 13

The preparation formula for crystalline form A capsule 1 is as follows:

| Formula | mg/capsule |
| --- | --- |
| Crystalline form A (Preparation Example 1) | 100 |
| Pregelatinized starch (Starch ® 1500) | 200 |
| Silica | 15 |
| Magnesium stearate | 4.5 |
| Total | 319.5 |

Process: (1) during passing the crystalline form A through a 100-mesh sieve, it was found that the sieving was difficult to perform, and much residue remained; after the sieving, much static electricity was produced; (2) pregelatinized starch and silica were passed through an 80-mesh sieve and then mixed with the crystalline form A in a zipper bag for 5 min; (3) magnesium stearate was passed through a 80-mesh sieve and then mixed with the powder mixture above in a zipper bag for 1 min; (4) 0 # gelatin capsules were filled with the resulting mixture manually.

The detection results show that the capsules of this example have an angle of repose of 32.91°, which is close to the fluidity data of the hydrate in the crystalline form D measured in Example 1.

Example 14

Preparation of Crystalline Form A Capsule 2

The formula of Example 13 was adopted again and the process below was used: (1) when the crystalline form A, together with pregelatinized starch, was passed through a 80-mesh sieve, the sieving results were somewhat improved but still not ideal, and much static electricity was produced; (2) silica was passed through an 80-mesh sieve and then mixed with the powder mixture above in a zipper bag for 3 min; (3) magnesium stearate was passed through a 80-mesh sieve and then mixed with the powder mixture above in a zipper bag for 1 min; (4) 0 # gelatin capsules were filled with the resulting mixture manually.

The detection results show that the capsules of this example have an angle of repose of 32.88°, which is close to the fluidity of the hydrate in the crystalline form D of Example 5. Influencing factor experiments were further conducted.

Example 15

The preparation formula for capsules of the hydrate in the crystalline form D is as follows, no other auxiliary materials involved:

| Formula | mg/capsule |
| --- | --- |
| Crystalline form D (Example 1) | 100 |

Process: (1) a formula amount of the hydrate in the crystalline form D prepared in Example 1 was taken and passed through an 80-mesh sieve; (2) 3 # gelatin capsules were filled, the starting materials were gently leveled, and capsule lids were put on; influencing factor experiments were conducted.

Example 16

Influencing Factor Experiments
A. High-Temperature Test 100 capsules of the products of Examples 14 and 15 were placed in an open Petri dish in an incubator at 60° C., and samples were taken at days 5 and 10. The characteristics and appearance were observed, the related substances were detected, and the content was determined.

B. High-Humidity Test 100 capsules of the products of Examples 14 and 15 were placed in an open Petri dish in a closed container with a relative humidity of 90±5% (saturated solution of potassium nitrate), and samples were taken at days 5 and 10. The characteristics and appearance were observed, the related substances were detected, and the content was determined.

C. Intense Light Irradiation Test 100 capsules of the products of Examples 14 and 15 were placed in an open Petri dish and irradiated using a 4500±500 LX fluorescent lamp, and samples were taken at days 5 and 10. The characteristics and appearance were observed, the related substances were detected, and the content was determined. The results are summarized below:

The results of the influencing factor experiments of the crystalline form A capsules of Example 14

| Time/conditions | | Appearance (Contents) | MCL % | Related substances Other impurities % |
|---|---|---|---|---|
| Day 0 | | Off-white fine powder | 0.00991 | 0.00846 |
| Day 5 | Intense light | Off-white fine powder | 0.01179 | 0.00873 |
| | High humidity | Off-white fine powder | 0.01617 | 0.01136 |
| | 60° C. | Off-white fine powder | 0.01725 | 0.00934 |
| Day 10 | Intense light | Off-white fine powder | 0.04447 | 0.00977 |
| | High humidity | Off-white fine powder | 0.04271 | 0.08056 |
| | 60° C. | Off-white fine powder | 0.13410 | 0.01245 |

The results of the influencing factor experiments of the capsules of the hydrate in the crystalline form D of Example 15

| Time/conditions | | Appearance (Contents) | MCL % | Related substances Other impurities % | Content % |
|---|---|---|---|---|---|
| Day 0 | | Off-white solid | 0.00300 | 0.01989 | Acceptable |
| Day 5 | High humidity | Off-white solid | 0.00250 | 0.01814 | Acceptable |
| | 60° C. | Off-white solid | 0.00912 | 0.01977 | Acceptable |
| | Intense light | Off-white solid | 0.00253 | 0.02020 | Acceptable |
| Day 10 | High humidity | Off-white solid | 0.00253 | 0.01918 | Acceptable |
| | 60° C. | Off-white solid | 0.01154 | 0.02050 | Acceptable |
| | Intense light | Off-white solid | 0.00856 | 0.02046 | Acceptable |

The results above show that under similar fluidity, in the influencing factor experiments of the capsules of the hydrate in the crystalline form D, the MCL (micheliolide) content did not significantly change within 5 days, while in the experiments of the crystalline form A capsules, the MCL content significantly increased after 5 days or more. Therefore, due to the excellent fluidity, the hydrate in the crystalline form D can be prepared into capsules without adding auxiliary materials and clinically applied. For the crystalline form A, however, it has significantly poorer stability than the crystalline form D even if the fluidity of its capsules has been improved by adding auxiliary materials and optimizing the process. Therefore, the capsules of the hydrate in the crystalline form D are superior to the crystalline form A capsules in terms of whether preparation process, stability or compliance.

The invention claimed is:

1. A hydrate of dimethylaminomicheliolide fumarate, wherein the hydrate is in a crystalline form D, the molar ratio of dimethylaminomicheliolide fumarate to water is 1:1, and the hydrate has a molecular formula of $C_{17}H_{27}NO_3 \cdot C_4H_4O_4 \cdot H_2O$; a thermogravimetric analysis of the hydrate shows a weight loss of 3.97%-4.22% before decomposition; and a differential scanning calorimetry pattern of the hydrate shows a dehydration endothermic peak at 75±5° C. and a characteristic melting peak at 148±5° C.

2. The hydrate of dimethylaminomicheliolide fumarate according to claim 1, wherein, the hydrate has characteristic peaks at 2θ angles of 7.8±0.2°, 11.1±0.2°, 11.4±0.2°, 12.6±0.2°, 12.9±0.2°, 14.4±0.2°, 15.3±0.2°, 17.0±0.2°, 18.7±0.2°, 19.7±0.2°, 20.6±0.2°, 21.0±0.2°, 22.5±0.2°, 23.7±0.2°, 24.3±0.2°, 25.5±0.2° and 26.2±0.2° in an X-ray powder diffraction pattern using Cu-Kα radiation, wherein the peak at 7.8±0.2° is an initial peak; the characteristic peak at 20.6±0.2° has a relative intensity of 100%; the crystalline form D is in an orthorhombic crystal system and has a space group of P2$_1$2$_1$2$_1$, a cell parameter of a=8.8346(18) Å, b=14.796(3) Å, c=16.385(3) Å, α=90°, β=90°, and γ=90°; and a cell volume of 2141.8(8) Å3.

3. The hydrate of dimethylaminomicheliolide fumarate according to claim 1, wherein, the hydrate also has characteristic peaks at 2θ angles of 10.5±0.2°, 11.7±0.2°, 12.0±0.2°, 15.6±0.2°, 15.9±0.2°, 16.2±0.2°, 21.3±0.2°, 22.1±0.2°, 23.0±0.2°, 26.4±0.2°, 27.2±0.2°, 28.2±0.2°, 28.6±0.2°, 29.3±0.2°, 30.4±0.2° and 31.1±0.2° in an X-ray powder diffraction pattern using Cu-Kα radiation.

4. A preparation method for the hydrate of dimethylaminomicheliolide fumarate according to claim 1, comprising:
under the action of stirring, adding dimethylaminomicheliolide and fumaric acid to a mixed solvent system of a solvent S1 and a solvent S2 at a constant temperature of 30° C.-70° C., with the mass ratio of the solvent S2 to the solvent S1 being (0-3):1 and the molar ratio of dimethylaminomicheliolide to fumaric acid being (1-1.6):1; and
after 5-10 h of reaction, filtering the reaction mixture and drying the residue at 25-45° C. under normal pressure for 6-10 h to obtain dimethylaminomicheliolide fumarate in a crystalline form D,
wherein:
the solvent S1 is a mixed solvent of water and one solvent selected from acetone, tetrahydrofuran, 1,4-dioxane, acetonitrile, and methyl isobutyl ketone;
the solvent S2 is a mixed solvent of an ester solvent and an ether solvent;

the ester solvent is selected from methyl acetate, ethyl acetate, hexyl acetate, isopropyl acetate, and a mixture of two thereof; and the ether solvent is selected from diethyl ether, methyl ethyl ether, methyl tert-butyl ether, dipropyl ether, dibutyl ether, ethylene glycol dimethyl ether, ethylene glycol monomethyl ether, 1,4-dioxane, tetrahydrofuran, 2-methyl tetrahydrofuran, and a mixture of two thereof.

5. The preparation method for the hydrate of dimethylaminomicheliolide fumarate according to claim 4, wherein:
in the solvent S1, the mass ratio of acetone, tetrahydrofuran, 1,4-dioxane, acetonitrile, or methyl isobutyl ketone to water in the solvent S1 is (5-10):1;
in the solvent S2, the mass ratio of the ester solvent to the ether solvent in the solvent S2 is (1-3):1; and
the mass ratio of the solid starting material dimethylaminomicheliolide to the solvent S1 is 1:(6-10).

6. A method for preparing a solventless compound of dimethylaminomicheliolide fumarate in a crystalline form B, comprising: heating the hydrate of dimethylaminomicheliolide fumarate of claim 1 at a constant temperature of 80° C.-120° C. for 10 min-30 min to obtain the solventless compound of dimethylaminomicheliolide fumarate in the crystalline form B.

7. A pharmaceutical composition, comprising: the hydrate of dimethylaminomicheliolide fumarate according to claim 1, a pharmaceutically acceptable auxiliary material and one, two, or more pharmacologically active ingredients other than the hydrate of dimethylaminomicheliolide fumarate.

8. The pharmaceutical composition according to claim 7, wherein the pharmaceutically acceptable auxiliary material further comprises a carrier or excipient selected from a filler, a glidant, a lubricant, a binder, and a stabilizer,
wherein the filler is selected from maize starch, glucose, mannitol, sorbitol, silica, microcrystalline cellulose, sodium carboxymethyl starch, composite starch, pregelatinized starch and mixtures thereof;

the glidant is selected from silica, hydrated silica, light anhydrous silicic acid, dry aluminum hydroxide gel, aluminum silicate, magnesium silicate, and mixtures thereof; and the lubricant is selected from wheat starch, rice starch, maize starch, stearic acid, calcium stearate, magnesium stearate, hydrated silica, light anhydrous silicic acid, synthetic aluminum silicate, dry aluminum hydroxide gel, talc, magnesium aluminometasilicate, dicalcium phosphate, anhydrous dicalcium phosphate, sucrose fatty acid esters, paraffins, hydrogenated vegetable oil, polyethylene glycol, and mixtures thereof.

9. A pharmaceutical preparation comprising: the pharmaceutical composition according to claim 7, wherein the pharmaceutical preparation is in a tablet, capsule or granule dosage form.

10. A medicament for treating a disease or condition, comprising the hydrate of dimethylaminomicheliolide fumarate according to claim 1, wherein the disease or condition is cancer selected from leukemia, breast cancer, prostate cancer, nasopharyngeal cancer, large intestine cancer, lung cancer, liver cancer, esophageal cancer, gastric cancer, intestinal cancer, renal cancer, oral cancer, Hodgkin's lymphoma, pancreatic cancer, colorectal cancer, cervical cancer, non-Hodgkin's lymphoma, glioma, melanoma, bladder cancer, ovarian cancer, thyroid cancer, and Kaposi's sarcoma.

11. A medicament for treating a disease or condition, comprising the pharmaceutical composition according to claim 7, wherein the disease or condition is cancer selected from leukemia, breast cancer, prostate cancer, nasopharyngeal cancer, large intestine cancer, lung cancer, liver cancer, esophageal cancer, gastric cancer, intestinal cancer, renal cancer, oral cancer, Hodgkin's lymphoma, pancreatic cancer, colorectal cancer, cervical cancer, non-Hodgkin's lymphoma, glioma, melanoma, bladder cancer, ovarian cancer, thyroid cancer, and Kaposi's sarcoma.

* * * * *